(12) United States Patent
Zimmon (10) Patent No.: US 6,315,733 B1
(45) Date of Patent: Nov. 13, 2001

(54) APPARATUS AND METHOD FOR CONTINUOUS MEASUREMENT OF PORTAL BLOOD PRESSURE

(75) Inventor: David S. Zimmon, Port Washington, NY (US)

(73) Assignee: Zimmon Science Corp., Port Washington, NY (US)

( * ) Notice: Subject to any disclaimer, the term of this patent is extended or adjusted under 35 U.S.C. 154(b) by 0 days.

(21) Appl. No.: 09/484,406

(22) Filed: Jan. 14, 2000

(51) Int. Cl.[7] ................................. A61B 5/02; A61B 5/00

(52) U.S. Cl. ..................... 600/486; 600/485; 600/481; 600/500; 600/561; 600/593

(58) Field of Search ........................... 600/486, 485, 600/488, 484, 483, 481, 437, 454, 466, 470, 407, 462, 500, 561, 593; 604/93, 96, 97, 98

(56) References Cited

U.S. PATENT DOCUMENTS 3,055,371 * 9/1962 Kulick ........................... 600/192
4,214,593 * 7/1980 Imbruce et al. ................. 600/561

(List continued on next page.)

OTHER PUBLICATIONS

Philippe Gertsch et al. (1993) Manometry of Esophageal Varices: Comparison of an Endoscopic Balloon Technique with Needle Puncture, Gastroenterology, vol. 105, pp. 1159–1166.

S.K. Sarin et al. (1989) Predictors of variceal bleeding: an analysis of clinical, endoscopic, and haemodynamic variables, with special reference to intravariceal pressure, Gut, vol. 30, pp. 1757–1764.

J. Polio et al. (1987) Critical Evaluation of a Pressure–Sensitive Capsule for Measurement of Esophageal Varix Pressure, Gastroenterology, vol. 92, pp. 1109–1115.

Joaquin Rigau et al. (1989) Endoscopic Measurement of Variceal Pressure in Cirrhosis: Correlation with Portal Pressure and Variceal Hemorrhage, Gastroenterology, vol. 96, pp. 873–880.

Daphna Fenyves et al. (1988) Intrahepatic Pressure Measurement: Not an Accurate Reflection of Portal Vein Pressure, Hepatology, vol, 8, No. 2, pp. 211–216.

Jaime Bosch et al. (1986) Noninvasive Measurement of the Pressure of Esophageal Varices Using an Endoscopic Gauge: Comparison with Measurements by Variceal Puncture in Patients Undergoing Endoscopic Sclerotherapy, Hepatology, vol. 6, No. 4, pp. 667–672.

Roger Mosimann, MD (1982) Nonaggressive Assessment of Portal Hypertension Using Endoscopic Measurement of Variceal Pressure, The American Journal of Surgery, vol. 143, pp. 212–214.

*Primary Examiner*—John P. Lacyk
*Assistant Examiner*—Navin Natnithithadha
(74) *Attorney, Agent, or Firm*—Collard & Roe, P.C.

(57) ABSTRACT

A method and a device for the intermittent or continuous measurement of portal blood pressure using a tamponade balloon inserted into the esophagus and stomach and a sensor positioned on the bridle, tamponade shaft or esophageal balloon. The tamponade balloons mounted over a tube are placed across the diaphragmatic hiatus and are gradually inflated through a lumen that runs from the balloons to a position that is external from the patient. The measured pressure within the tamponade is increased until the blood flow in the collateral portal veins that traverse the diaphragm are occluded. The cessation of the blood flow into the esophageal varices is signaled when the sensor identifies a change in diameter of the varices, a change in the color of the esophageal wall, or a change in velocity of blood flow. The measured tamponade pressure at the nadir of variceal blood flow is equivalent to portal blood pressure.

12 Claims, 8 Drawing Sheets

U.S. PATENT DOCUMENTS

| | | | |
|---|---|---|---|
| 4,367,747 | * | 1/1983 | Witzel .................................... 604/99 |
| 4,735,194 | * | 4/1988 | Stiegmann ........................... 600/194 |
| 4,832,691 | * | 5/1989 | Witzel .................................... 604/96 |
| 4,981,470 | * | 1/1991 | Bombeck, IV ...................... 600/350 |
| 5,048,532 | * | 9/1991 | Hickey ................................. 600/488 |
| 5,181,517 | * | 1/1993 | Hickey ................................. 600/486 |
| 5,247,938 | * | 9/1993 | Silverstein et al. .................. 600/485 |
| 5,263,485 | * | 11/1993 | Hickey ................................. 600/486 |
| 5,308,326 | | 5/1994 | Zimmon . |
| 5,398,692 | * | 3/1995 | Hickey ................................. 600/486 |
| 5,551,439 | * | 9/1996 | Hickey ................................. 600/486 |
| 5,570,671 | * | 11/1996 | Hickey ................................. 600/486 |
| 5,653,240 | | 8/1997 | Zimmon . |
| 5,785,684 | | 7/1998 | Zimmon . |
| 5,921,935 | * | 7/1999 | Hickey ................................. 600/485 |
| 6,120,442 | * | 9/2000 | Hickey ................................. 600/300 |

* cited by examiner

APPARATUS AND METHOD FOR CONTINUOUS MEASUREMENT OF PORTAL BLOOD PRESSURE

BACKGROUND OF THE INVENTION

1. Field of the Invention

This invention pertains to a method and a device for the continuous measurement of portal blood pressure. The method and device use an inflatable tamponade balloon inserted into the esophagus and a sensor to monitor the portal blood pressure.

2. The Prior Art

U.S. Pat. No. 5,653,240 to Zimmon, the disclosure of which is herein incorporated by reference, discloses a method and device for measuring portal blood pressure. That invention provides a device and a technically simple method for measuring portal venous pressure in patients with esophageal varices and or portal systemic collateral veins during upper gastrointestinal endoscopy or without endoscopy by positioning the tamponade and sensor with an instrument passed from the mouth into the stomach to provide a rail for introduction and removal. These instruments include an oral-gastric tube, balloon introducer, wire guided dilator, bougie or other similar device. The oral-gastric tube method allows the measurement of portal pressure after tamponade for bleeding without the need for expensive and technically demanding gastrointestinal endoscopy. Such measurements are essential to evaluate the patient's response to drug therapy and determine the therapeutic action required for prevention of recurrent bleeding. An advantage of the above mentioned invention is that in the non-bleeding patient, it allows endoscopic surveillance of esophageal varices combined with measurement of portal venous pressure as a single procedure using only conscious sedation.

However, the use of a large endoscope such as used in the patent mentioned above to observe the collapse of esophageal varices is cumbersome and difficult for the patient, since it requires sedation. It would be desirable to find a method for measuring portal blood pressure that eliminates the need for endoscopy and makes the use of tamponade with sensors available to those without endoscopic skills.

Furthermore there have been numerous endoscopic attempts to measure portal pressure or pressure in esophageal varices. These methods are cumbersome and fail because of the difficulty of identifying the collapse of esophageal varices. The problem is increased when the varices are small. The visual endoscopic methods are limited to operators with considerable endoscopic skill and accept the disabilities of esophageal peristalsis and the need to inflate the esophagus with air that both provokes peristalsis and raises intra-esophageal pressure to limit the accuracy of measurement. This is in contrast to the tamponade method that provides a deflated stomach for continuous esophageal decompression through an esophagogastric sphincter that is breached by the tamponade lumen. Methods requiring needle puncture of varices accept the risk or hemorrhage and are of necessity performed only when endoscopic injection sclerosis of varices in indicated and necessary. Otherwise the risk of bleeding from varix puncture or late bleeding from ulceration associated with varix sclerosis would not be acceptable. All of these esophageal methods measure pressure during continuous flow of blood in the varices in a resistance loop between the portal circulation and a central outflow site that is a derivative pressure. Since the precise site of measurement and its position in the resistance loop is not known, the relationship of the measured pressure to intra-abdominal portal pressure cannot be known and the measurement cannot be reproducible.

REFERENCES

1. Moismann R. Nonaggressive assessment of portal hypertension using endoscopic measurement of variceal pressure. American J Surgery 1982;143:212–214.
2. Bosch J. et al. Noninvasive measurement of the pressure of esophageal varices using an endoscopic gauge: comparison with measurements by variceal puncture in patients undergoing endoscopic sclerotherapy. Hepatology 1986;6:667–672.
3. Fenyves D. et al. Intrahepatic pressure measurement: not an accurate reflection of portal vein pressure. Hepatology 1988;8:211–216.
4. Rigau J. et al. Endoscopic measurement of variceal pressure in cirrhosis: correlation with portal pressure and variceal hemorrhage. Gastroenterology 1989;96:873–880.
5. Polio J. et al. Critical evaluation of a pressure-sensitive capsul for measurement of esophageal varix pressure. Gastroenterology 1987;92:1109–1115.
6. Sarin SK. et al. Predictors of variceal bleeding: an analysis of clinical, endoscopic and haemodynamic variables with special reference to intravariceal pressure. Gut 1989;30:1757–1764.
7. Gertsch P. et al. Manometer of esophageal varices: comparison of an endoscopic balloon technique with needle puncture. Gastroenterology 1993;105:1159–1166.

SUMMARY OF THE INVENTION

It is therefore an object of the present invention to provide a device and a technically simple method for the continuous measurement of portal pressure during balloon tamponade using sensors as alternatives to standard endoscopic techniques.

These and other objects are accomplished by a device for measuring portal blood pressure comprising a tube with proximal and distal open ends, an esophageal inflatable balloon mounted over the tube, a first inflation lumen opening into the esophageal inflatable balloon for directing pressurized fluid to inflate the esophageal inflatable balloon, a gastric inflatable balloon mounted over the tube between the esophageal inflatable balloon and the distal open end, a second inflation lumen opening into the gastric inflatable balloon for directing pressurized fluid to inflate the gastric balloon, and a non-visual sensor mounted on the esophageal balloon or a small endoscope or video camera that is inserted through the tube, to detect the changes resulting from tamponade.

The invention also comprises a method of measuring the portal pressure by backloading the device on an endoscope by passing the endoscope through the open ends of the tube, passing the endoscope down the esophagus advancing the device along the endoscope and down the esophagus to a location within the diaphragmatic hiatus, positioning the gastric balloon inside the stomach and inflating the gastric balloon, pulling the balloon against the proximal stomach and the diaphragmatic hiatus with a traction means to seat the gastric balloon against the gastric cardia, inflating the esophageal inflatable balloon to fix the device across the diaphragmatic hiatus by the two opposed balloons, releasing the traction means, locating the sensor to a position above or adjacent to the esophageal inflatable balloon, to observe esophageal varices, gradually inflating the balloons until blood flow in the portal veins traversing the diaphragmatic hiatus occludes, so that the esophageal varices collapse or blood flow ceases or is reduced to a nadir as detected by said sensor, and monitoring the pressure inside said esophageal inflatable balloon and gastric inflatable balloon as sensed by the sensor to obtain an indication of the portal blood pressure. By serially inflating and deflating the balloons while monitoring the state of blood flow in the varices, portal pressure is measured continuously in a fashion similar to automated systemic blood pressure monitoring.

The device preferably also includes a bridle attached to the tube to extend up the esophagus to a traction means. The bridle is manipulated to position the proximal end of the device within the digestive tract and maintain the device in traction.

In addition, an aspiration tube is positioned within the stomach and a fluid supply tube is positioned adjacent to the esophageal balloon. The gastric aspiration tube and lumen of the tamponade device serves the important function of continuously reducing gastric and distal esophageal pressure to ambient pressure. Otherwise the continued swallowing of air and saliva combined with esophageal peristalsis would raise the esophageal pressure and bias the measurement of portal pressure. Similarly the tamponade lumen allows emptying of the esophagus into the stomach to prevent the risk and discomfort of esophageal obstruction. The patient does not perceive an inflated tamponade in the distal esophagus. Consequently portal pressure can be measured over a prolonged period by sequentially inflating and deflating the tamponade.

For this purpose, deaerated fluid is gradually infused adjacent to the esophageal balloon while aspirating the stomach.

The stomach is aspirated and the fluid is infused adjacent to the esophageal balloon while deflating the esophageal inflatable balloon and gastric inflatable balloon until the esophageal varices distend or blood flow increases as determined by the sensor. The pressure within the balloons is then measured via by a second sensor.

Repeated measurements would be useful in monitoring portal pressure during the administration of drugs for the control of portal hypertension, particularly in patients with active or recent bleeding. The efficacy of drug therapy in reducing portal pressure must be determined to identify patients who can be spared other interventions. Conversely, patients who fail to respond to drug therapy with a sufficient decrease in portal pressure, which reduces the risk of hemorrhage, would require alternative therapy.

Blood flow in esophageal varices is rapid and produces bulging blue visible vessels in the esophageal wall. A sensor that identifies a change in diameter of the varices, such as an ultrasound probe; a change in the color of the esophageal wall when the blue vessels diminish in size, such as reflectance spectrometry as in oximetry; or a change in velocity of flow as indicated by temperature, electrical impedance or doppler ultrasound, could be used.

Improvements in endoscopes have allowed the development of 2 mm diameter battery powered endoscopes and small video cameras. Where electronic measurements or endoscopic ultrasound probes that require complex electrical monitoring devices are not available, a small endoscope or video camera can serve to identify varix collapse when placed through the patient's nose to the appropriate site above the tamponade. This endoscope could be used in conjunction with the present invention to visualize whether the varices are expanded and visible or collapsed and tamponade pressure adjusted to obtain a pressure measurement. Similar periodic measurements would similarly be made using the sensors described.

The preferred method for measuring portal pressure would have a tamponade balloon such as that described in U.S. Pat. No. 5,308,326, the disclosure of which is herein incorporated by reference, an expandable compression disc or other similar device located in the stomach and held in place by a similar device in the esophagus. A patent lumen connecting the esophagus and stomach to equalize pressure is important, since without such a lumen, swallowing and esophageal peristalsis periodically increases esophageal pressure to oppose variceal pressure and influences pressure and flow in esophageal varices.

A similar disability is present during routine endoscopic observation of varices in the esophagus since air inflation is essential to allow visualization of the varices. This is the distinct advantage of using a non-visual sensor since air pressure would not be required. Endoscopic visual measurement of varix collapse and refill is difficult or impossible when varices are small or absent. Non-visual sensors that penetrate the esophageal mucosa such as temperature, Doppler ultrasound, electrical impedance and the like have the advantage of identifying small esophageal varices and portal systemic collateral veins on the esophageal surface for portal pressure measurement before dilated esophageal veins can be appreciated by endoscopy.

The tamponade device must be provided with a bridle for introduction and communication with the balloon or compression discs as well as the sensor. This would be similar to the esophagogastric balloon tamponade device bridle described in U.S. Pat. No. 5,308,326, that is hereby incorporated by reference. With ultrasound or ultrasound doppler sensors, an additional source of fluid to couple the transducer to the esophageal wall is required. This is provided by a fine tube within or outside the bridle carrying a trickle of deaerated water or other fluid.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
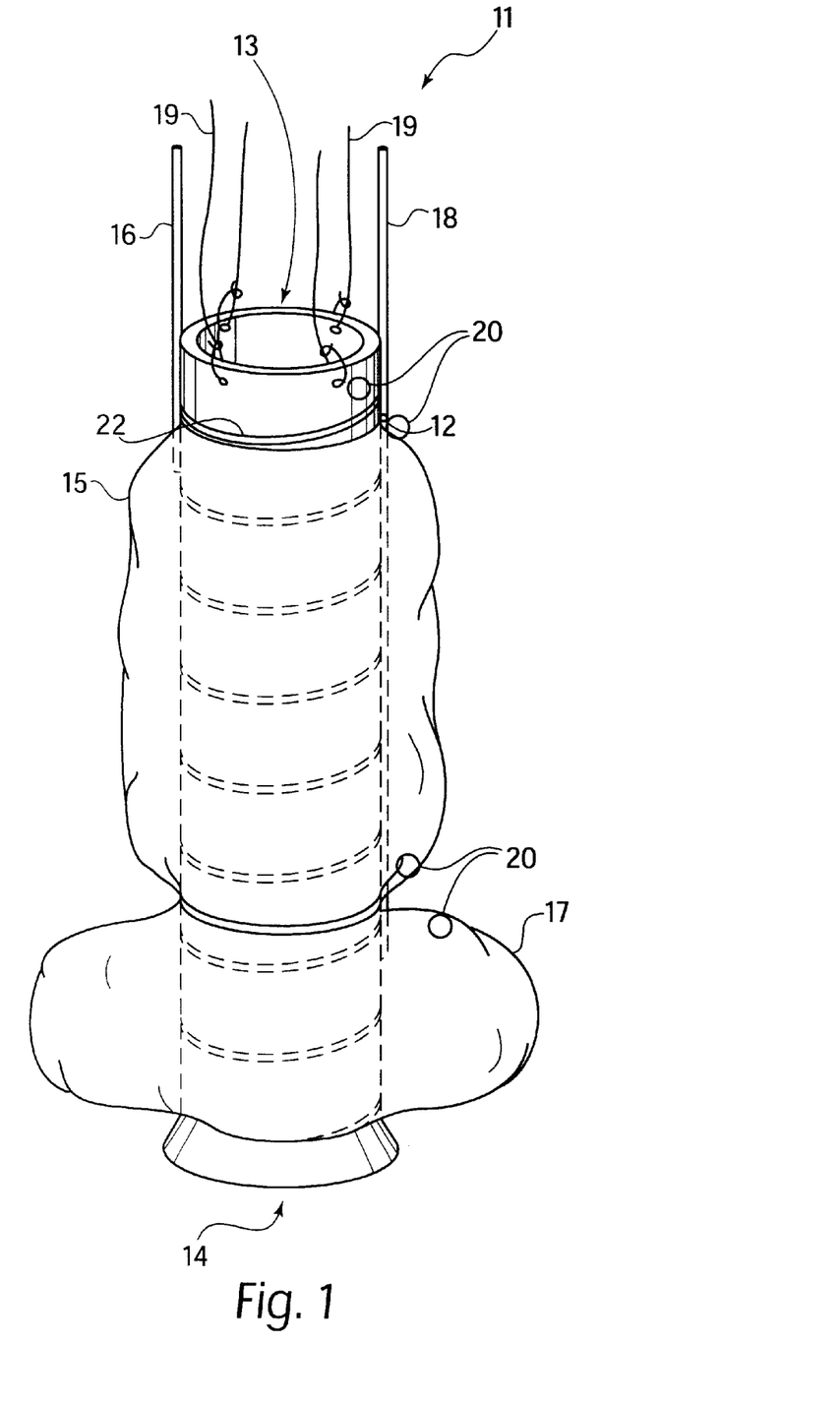
FIG. 1 is a perspective view of one embodiment of a device used to practice this invention, for illustrative purposes, the full lengths of the wires 19 and of the lumens 16 and 18 are not shown.

Referring now in detail to the drawings and, in particular, FIG. 1 a preferred esophago-gastric balloon device 11 is shown. The device 11 includes an elongate member 12, preferably a tube, having a proximal end 13 and a distal end 14, where both ends are preferably open. An esophageal inflatable balloon 15 is mounted over the elongate member 12, and an inflation lumen 16 is provided for directing pressurized fluid in and out the esophageal inflatable balloon 15. A gastric inflatable balloon 17 is mounted over the elongate member 12 and is adapted to seat against the gastric cardia when inflated in the stomach, and when the device 11 is pulled by the wires 19 in a direction up the esophagus. A separate inflation lumen 18 is provided to inflate and deflate the gastric inflatable balloon 17.

The esophageal inflatable balloon 15 is mounted over the elongate member 12. As to the method of mounting the esophageal inflatable balloon over the tube, it may be mounted by silk ties, bonding or vulcanizing, or any other suitable airtight manner known in the art. An inflation lumen 16 for directing pressurized fluid to inflate the esophageal inflatable balloon 15 is also provided and preferably is bonded to the side of the elongate member 12.

The gastric inflatable balloon 17 is mounted over the elongate member 12 near its distal end 14 to provide a seating surface within the stomach. The gastric inflatable balloon 17 has an inflated diameter which is sufficiently large, so that when positioned in the stomach and inflated, the gastric inflatable balloon 17 seats against and compresses the gastric cardia when the device 11 is pulled by the wires 19, or pulled by the proximal end of the elongate member 12 in a direction up the esophagus. The gastric inflatable balloon 17 can be mounted using silk ties, bonding or vulcanizing, or any other suitable airtight method known in the art.

A non-visual sensor 20 is mounted to one of balloons 15 and 17 for measuring the pressure. Sensor 20 can be any one of a variety of sensors, such as a sensor that identifies a change in diameter of the varices, such as an ultrasound probe; a change in the color of the esophageal wall when the blue vessels diminish in size, such as reflectance spectrometry as in oximetry; or a change in velocity of flow as indicated by temperature, electrical impedance or doppler ultrasound. Sensor 20 can be mounted in any of a variety of positions on the device, depending on the type of sensor to be used. The various positions of sensor 20 are shown in FIGS. 2–8.

An inflation lumen is also provided to direct pressurized fluid to inflate the gastric inflatable balloon 17. This lumen could be the same one which inflates the esophageal inflatable balloon 15, but in a preferred device, a second and separate inflation lumen 18 is provided for the gastric inflatable balloon 17, and is also bonded to the side of the elongate member 12. The inflation lumen 18 passes through the esophageal inflatable balloon 15 and into the gastric inflatable balloon 17, opening only into the latter. This enables the selective inflation of the esophageal inflatable balloon 15 and the gastric inflatable balloon 17.

A preferred device 11 also includes a plurality of wires 19 which are attached to the elongate member 12 and generally form a bridle. In the preferred device 11, the wires 19 are of sufficient length that, when the device 11 is in place, the wires 19 extend up the esophagus and externally extend from the patient. Thus, the bridle is adapted and operable to allow the device 11 to be secured in place in the patient while having the proximal open end 13 of the elongate member 12 positioned within the esophagus. This provides a convenient passage through which materials may pass to the stomach and enables normal feeding and swallowing. The wires 19 are attached to the elongate member 12 by securing them through small apertures 20 provided near the proximal open end 13 of the elongate member 12.

It is understood, however, that bonding or any other suitable means known in the art could be used to attach the wires 19 to the elongate member 12.

As an initial step to practice this invention, the device is passed down the esophagus, to a location within the patient's stomach. The device is backloaded on the endoscope or oral-gastric tube by passing the endoscope or oral-gastric tube through the open ends of the device. The endoscope or tube is then passed through the patient's mouth, down the esophagus, and into the stomach, usually a distance of about 50 cm past the patient's incisors.

Figure 2:
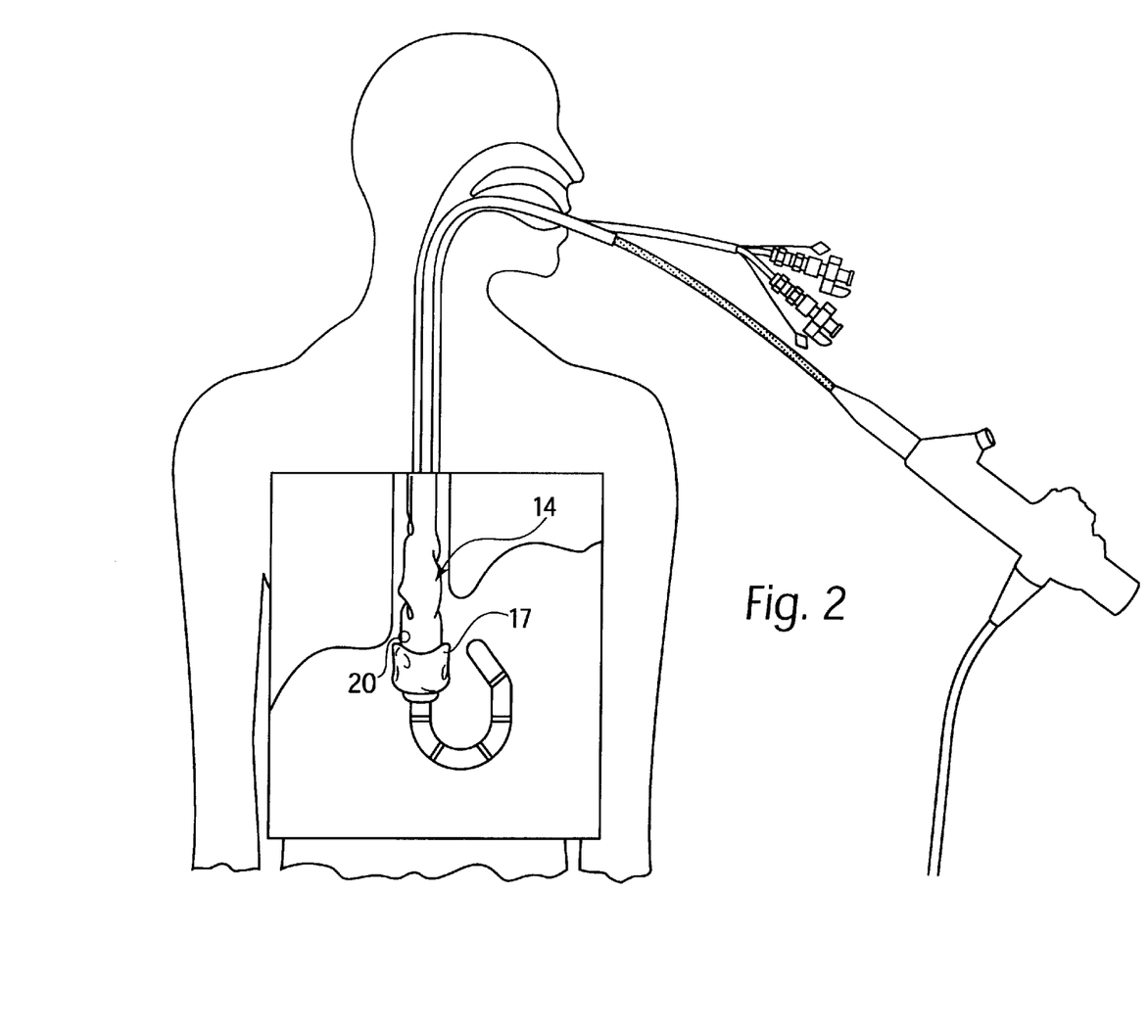
FIGS. 2 to 8 are step-by-step sectional views of the device illustrated in FIG. 1 being placed in a patient, according to one embodiment of this invention.

Next and referring to FIG. 2, the device 11 is advanced down over the endoscope using a split or unsplit overtube until the gastric inflatable balloon 17 is positioned within the stomach while leaving at least a portion of the bridle or the elongate member external to the patient.

Figure 3:
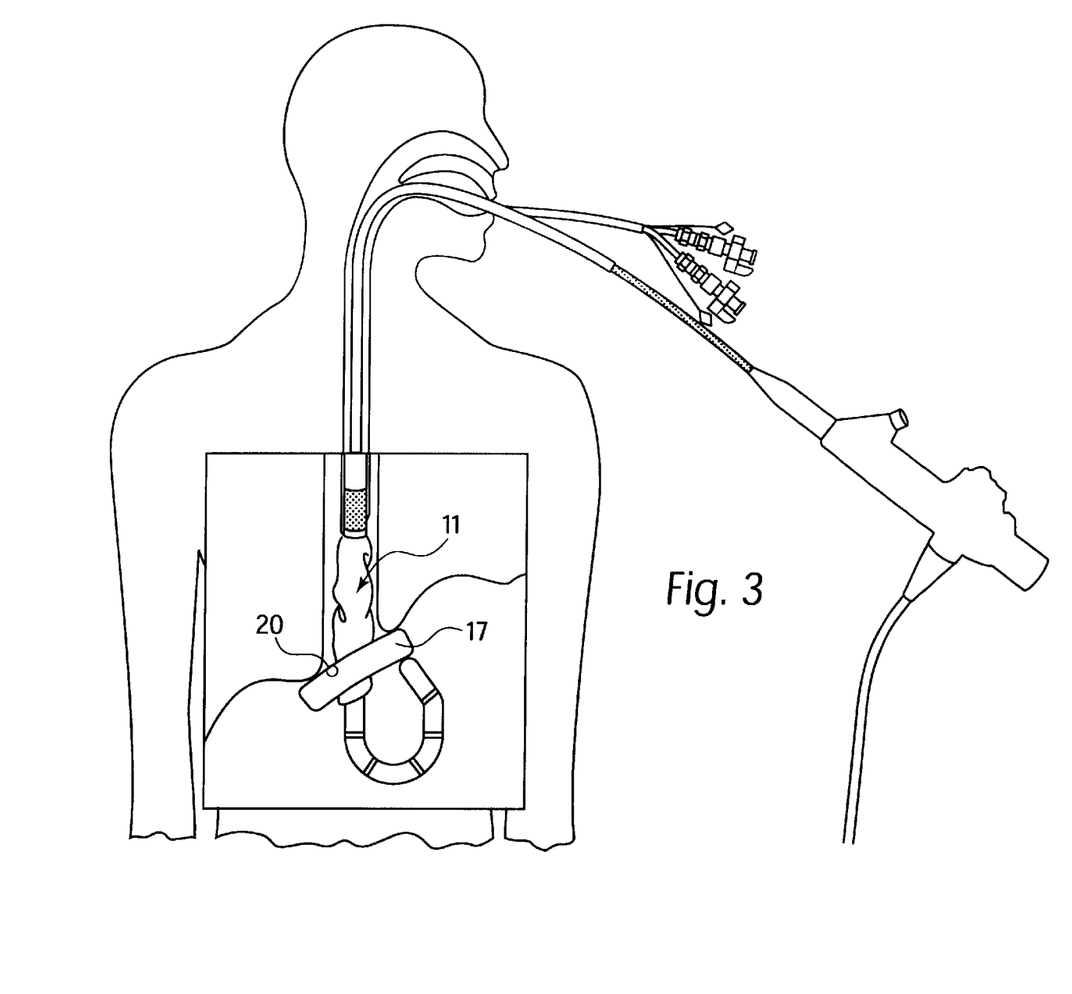

Referring to FIG. 3, the gastric inflatable balloon 17 is inflated and the elongate member pulled with the bridle wires until the gastric inflatable balloon is felt to seat against the gastric cardia. Once in position, the pressure within the gastric inflatable balloon is preferably adjusted to about 50 mmHg.

Figure 4:
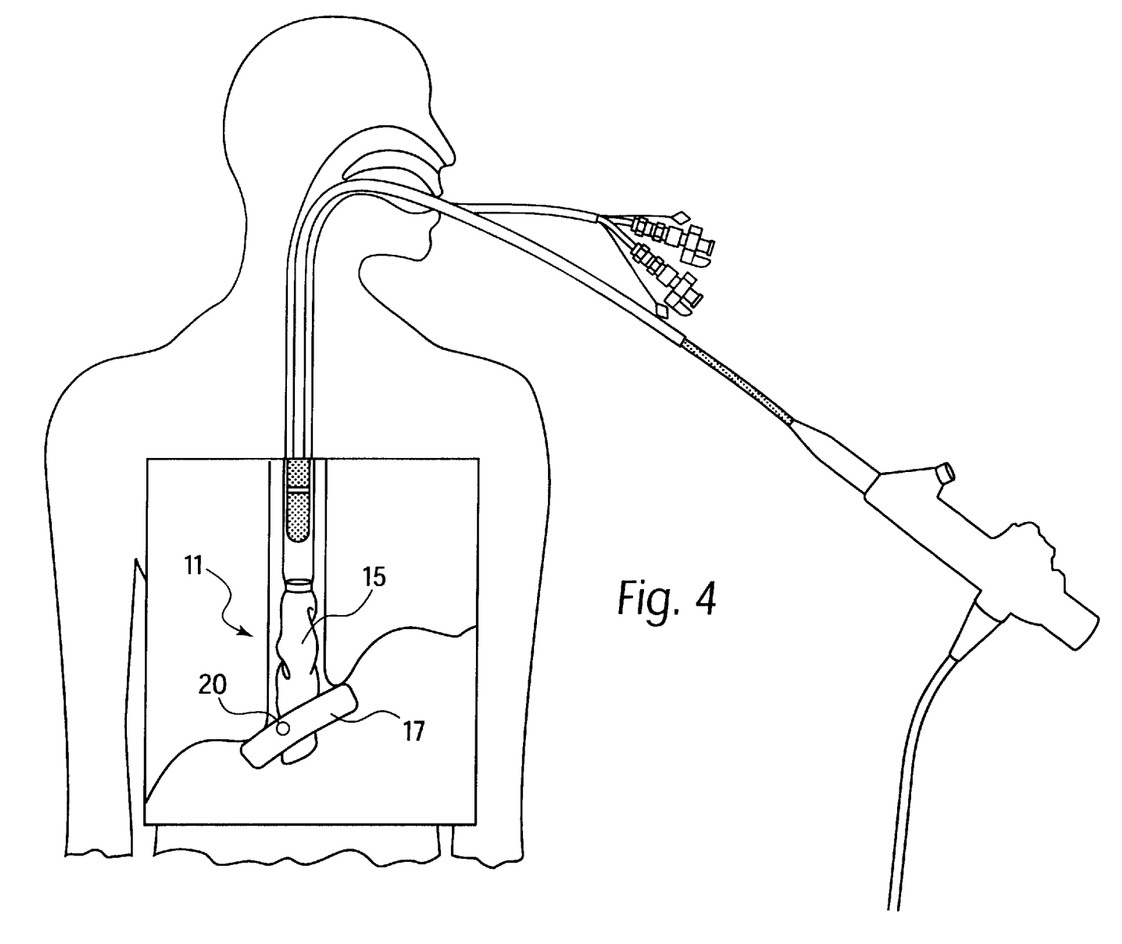

Referring to FIG. 4, after the inflation of the gastric inflatable balloon 17 and its placement against the gastric cardia, the pushing tube is withdrawn from the stomach to a location above the device 11.

Figure 5:
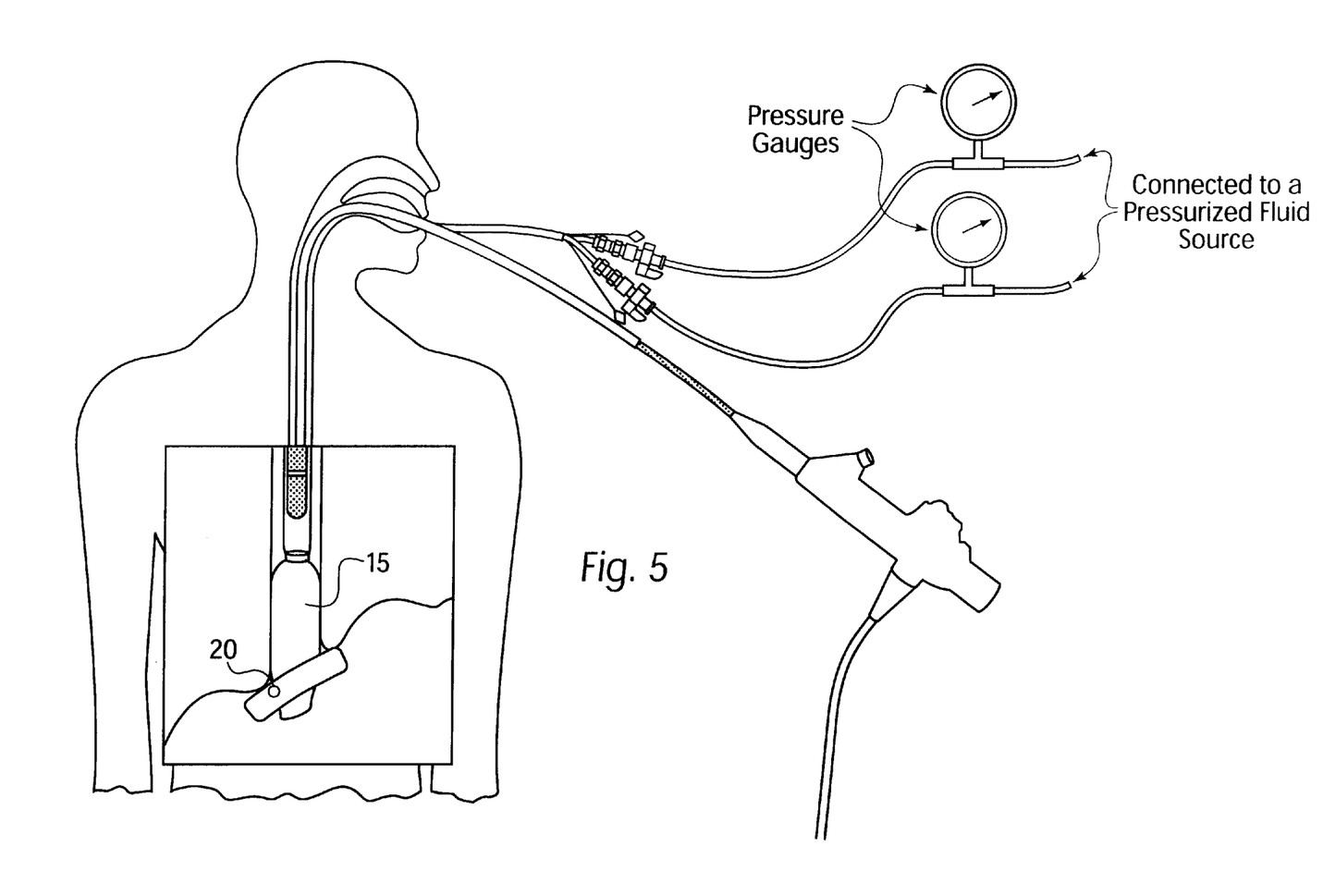

Referring to FIG. 5, the esophageal inflatable balloon 15 is then inflated to fix the device 11 into position by compressing the diaphragmatic hiatus and surrounding tissue. A preferable initial inflation pressure is about 50 mmHg. Once device 11 is fixed, the external pulling or traction to device 11 is then preferably released. The release of traction allows the patient's diaphragm to move in normal respiration which otherwise might prevent an accurate measure of the patient's portal blood pressure.

Once in position, the esophageal and gastric inflatable balloons are inflated and fixed into position by compressing the diaphragm and surrounding tissue from opposing sides of the diaphragm. The esophageal and gastric inflatable balloons are then further inflated and deflated, as needed, to measure portal blood pressure.

Figure 6:
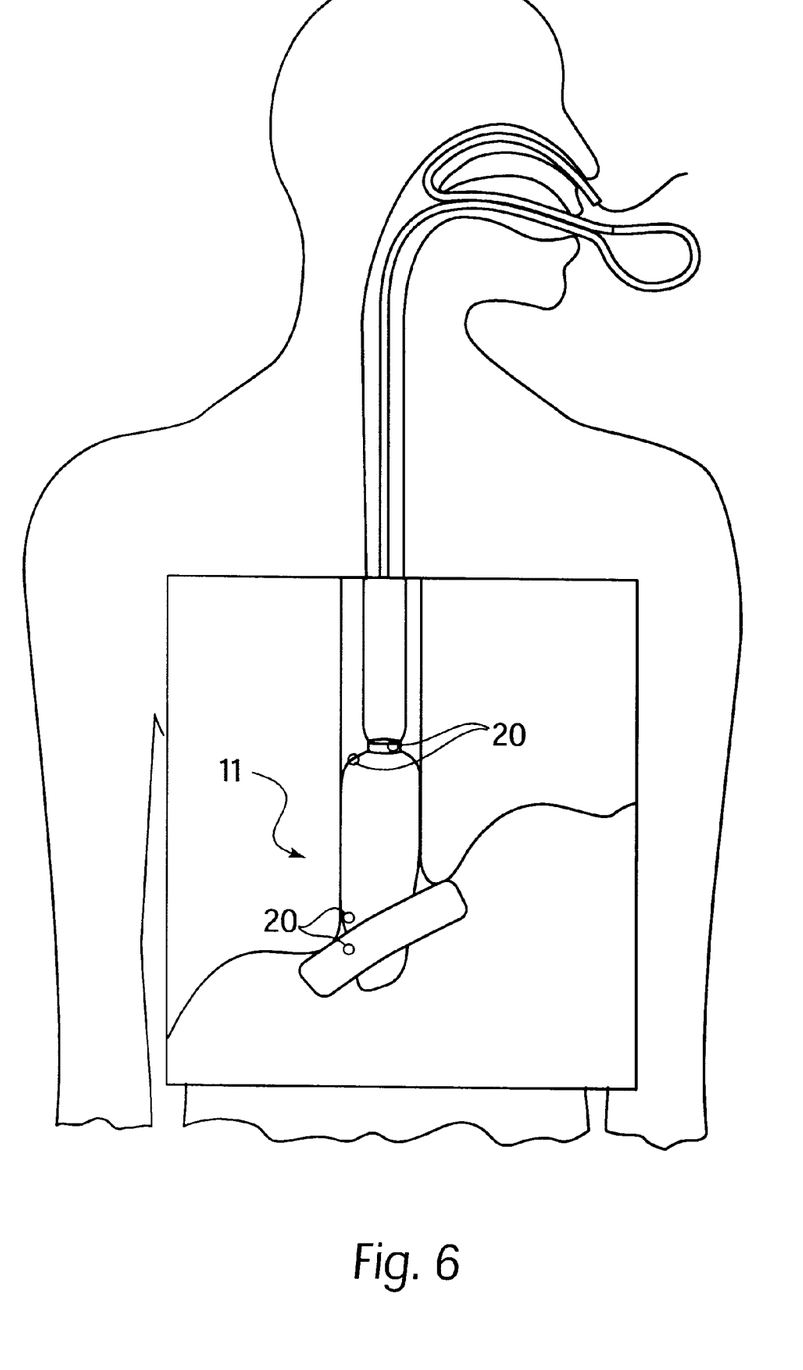
Figure 7:
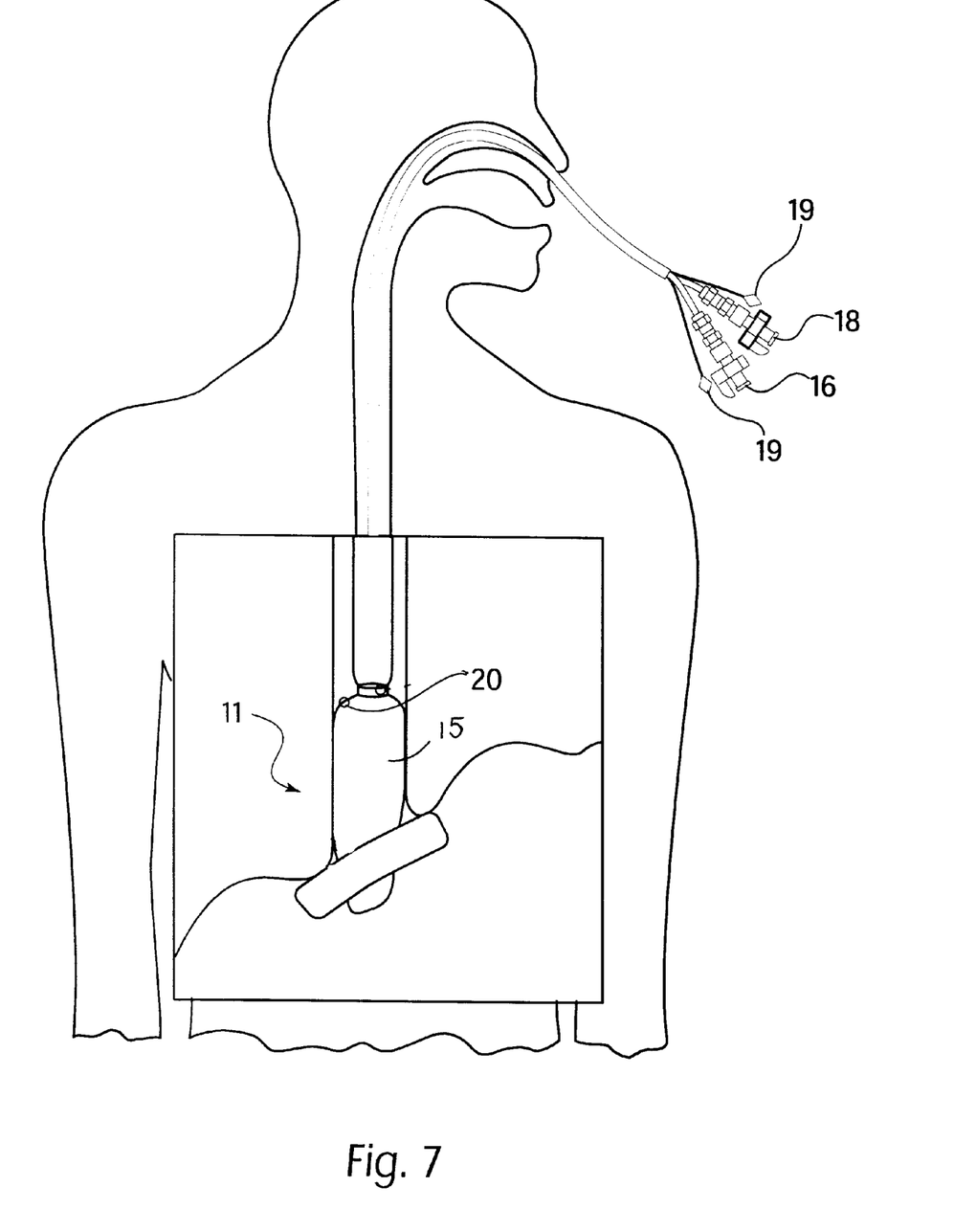

Additionally, prior to advancing the device down the esophagus, suitable hemostatic (such as microfibrillar collagen hemostat), coagulant (such as Thrombin, USP), or cytoprotective (such as sucralfate) substances can be applied to esophageal inflatable balloon 15 and/or gastric inflatable balloon 17. Such applications facilitate the later removal of the device by preventing adherence of the balloons to any bleeding sites. Referring to FIGS. 6 and 7, a preferred method for securing a bridle is shown. Once it has been confirmed that the device 11 is properly placed, a flexible guide tube having first and second open ends is provided. The first end of the guide tube is then placed through the nose and out the mouth of the patient, with the second end of the guide tube remaining external of the nose. Next, the bridle wires 19 and the inflation lumens 16 and 18, which are extending out of the mouth, are passed into said first end and out the second end of the guide tube. The guide tube is then withdrawn from the nose to leave bridle wires 19 and lumens 16 and 18 positioned through the patient's nose.

The established nasal bridle position is generally shown in FIG. 7. The gastric inflatable balloon 17 and the esophageal inflatable balloon 15 are inflated, and the wires 19 and the inflation lumens 16 and 18 are extending out of the nose. The appropriate connectors can then be placed on the inflation lumens 16 and 18 and the bridle wires 19 can be connected to a traction device as necessary. Having the lumens 16 and 18 and the bridle wires 19 positioned through the patient's nose increases patient comfort and reduces trauma to the nose and pharynx.

Figure 8:
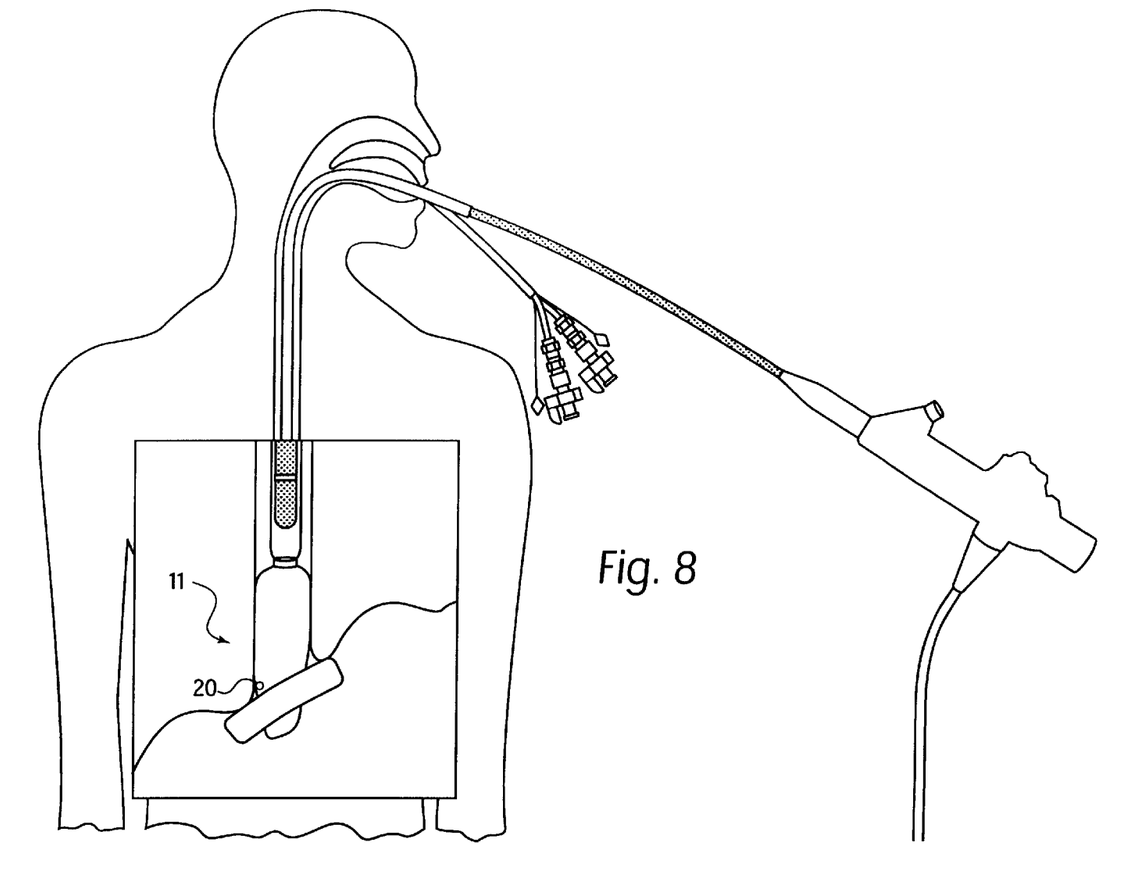

Referring to FIG. 8, the sensor measures the blood pressure as follows: pressure in the inflatable balloons is slowly reduced until the varices distend and reappear. Pressure is then increased in the inflatable balloons while monitoring the inflation pressure. When the pressure inside the inflatable balloons is high enough to occlude blood flow in the portal veins traversing the diaphragmatic hiatus, the varices above the esophageal inflatable balloon collapse. The balloon pressure required to occlude these portal collateral veins is about identical to the pressure in the main portal vein. Upon occlusion, the balloons may be deflated to allow the esophageal varices to distend and this pressure is also measured. The sensor identifies the change in diameter of the varices (using an ultrasound probe), a change in the color of the esophageal varices when the blue vessels diminish in size (using a reflectance spectrometry as in oximetry), or a change in velocity of flow as indicated by temperature, using electrical impedance or doppler ultrasound. Sensor 20 is preferably mounted on the esophageal balloon. However, sensor 20 could also be mounted on the endoscope.

Although a balloon is the preferred embodiment of this invention, it must be understood that similar functions could be served by any type of compression device including a disc or cage activated by gas pressure, a calibrated spring or any mechanical means.

Further details regarding the device can be found in Method and Device for Measuring Portal Blood Pressure, U.S. Pat. No. 5,653,240 which is incorporated into this specification by reference.

Accordingly, while only one embodiment of the present invention has been shown and described, it is obvious that many changes and modifications may be made thereunto without departing from the spirit and scope of the invention.

What is claimed is:

1. A method for the continuous measurement of portal blood pressure, comprising the steps of:
   providing a device having a tube with proximal and distal open ends, an esophageal inflatable balloon mounted over said tube, a first inflation lumen opening into said esophageal inflatable balloon for directing pressurized fluid to inflate said esophageal inflatable balloon, a gastric inflatable balloon mounted over said tube between said esophageal inflatable balloon and said distal open end, a second inflation lumen opening into said gastric inflatable balloon for directing pressurized fluid to inflate said gastric balloon, and a sensor attached to one of said balloons;
   backloading said device on an endoscope, oral-gastric tube or other tube introducer by passing the introducer through said open ends of said tube;
   passing the introducer down the esophagus;
   advancing said de vice along the introducer with a pusher down the esophagus to a location within the stomach;
   positioning said gastric balloon inside the stomach and inflating said gastric balloon;
   pulling said gastric balloon against the proximal stomach and the diaphragmatic hiatus with a traction means to seat said gastric balloon against the gastric cardia;
   inflating the esophageal inflatable balloon to fix said device across the diaphragmatic hiatus by the two opposed balloons;
   releasing said traction means;
   locating said sensor to a position above or adjacent to the esophageal inflatable balloon, to monitor esophageal varices;
   gradually inflating said balloons until blood flow in the portal collateral veins traversing the diaphragmatic hiatus occludes, whereby the esophageal varices collapse or blood flow ceases, or is reduced to a nadir as detected by said sensor; and
   monitoring the pressure inside said esophageal inflatable balloon and said gastric inflatable balloon to obtain an indication of the portal blood pressure as the tamponade pressure required to occlude portal collateral veins leading to the esophagus.

2. The method of claim 1, wherein said providing step further includes a bridle attached to said tube, said bridle adapted to extend up the esophagus to a traction means.

3. The method of claim 2, further comprising manipulating the bridle to position the proximal end of the member within the digestive tract and maintain the device in traction as required to maintain tamponade position when the diaphragmatic hiatus is large and would allow the esophageal balloon to descent into the stomach.

4. The method of claim 1, further comprising the step of positioning an aspiration tube within the stomach and a fluid supply tube adjacent to the esophageal balloon.

5. The method of claim 4, further comprising the step of gradually infusing deaerated fluid adjacent to the esophageal balloon while aspirating the stomach.

6. The method of claim 1, further comprising aspirating the stomach and infusing the fluid adjacent to the esophageal balloon while deflating said esophageal inflatable balloon and said gastric inflatable balloon until the esophageal varices distend or blood flow increases as determined by said sensor and measuring the pressure within said balloons as equal to the pressure in the portal collateral veins.

7. A device for continuously measuring portal blood pressure, comprising:
   a tube with proximal and distal open ends,
   an esophageal inflatable balloon mounted over said tube;
   a first inflation lumen opening into said esophageal inflatable balloon for directing pressurized fluid to inflate said esophageal inflatable balloon;
   a gastric inflatable balloon mounted over said tube between said esophageal inflatable balloon and said distal open end;
   a sensor mounted to one of said balloons for monitoring the pressure inside said balloons to obtain an indication of the portal blood pressure as the tamponade pressure required to occlude portal collateral veins;
   a second inflation lumen opening into said gastric inflatable balloon for directing pressurized fluid to inflate said gastric balloon; and
   a device to visually identify varix collapse with increasing tamponade pressure and refill with decreasing tamponade pressure;
   wherein said balloons are inflated until blood flow in the portal collateral veins traversing the diaphragmatic hiatus are occluded.

8. The device according to claim 7, further comprising a traction means to seat said gastric balloon against the gastric cardia.

9. The device according to claim 8, further comprising a bridle attached to the tamponade device and adapted to extend up the esophagus to a traction means.

10. The device according to claim 7, further comprising a monitor connected to said sensor for monitoring the tamponade pressure and blood flow in esophageal and adjacent veins sensed by said sensor.

11. The device according to claim 9, wherein the sensor is selected from the group consisting of sensors for identifying change in diameter of the varices, change in color of the esophageal varices, change in velocity of flow.

12. The device according to claim 11, further comprising a fine tube near the bridle carrying a trickle of deaerated water or other fluid across the sensor.

* * * * *